United States Patent [19]

Slessor et al.

[11] Patent Number: 4,990,331

[45] Date of Patent: Feb. 5, 1991

[54] NOVEL PHEROMONE COMPOSITION FOR USE IN CONTROLLING HONEY BEE COLONIES

[76] Inventors: Keith N. Slessor, 10105 Rolley Crescent, Whonnock, B.C., V2X 8X7; Lori-Ann Kaminski, 303 - 1771 East Georgia, Vancouver, B.C., V5L 2B3; Gaylord G. S. King, 305 - 561 Cottonwood Ave., Coquitlam, B.C., V3J 2R9; John H. Borden, 6552 Carnegie St., Burnaby, B.C., V5B 1Y3; Mark L. Winston, 302 Princess Street, New Westminster, B.C., V3L 1V5, all of Canada

[21] Appl. No.: 127,198

[22] Filed: Dec. 1, 1987

[51] Int. Cl.$^5$ .................... A01K 57/00; A01N 25/00
[52] U.S. Cl. .................................. 424/84; 449/1; 449/2; 514/544; 514/560
[58] Field of Search ............... 514/544, 560; 424/84; 449/1, 2

[56] References Cited

FOREIGN PATENT DOCUMENTS 60-184045 9/1985 Japan .
2095988 10/1982 United Kingdom .

OTHER PUBLICATIONS

Chemical Abstract No. CA111(21): 191772w, Crewe et al., Z. Naturforsch., C: Biosci. 44(7-8), 590-6 (1989).
Chemical Abstract No. CA 111(3): 21131u, Movitz et al., Apidologie, 19(4) 333-42 (1988).
Anderson et al., CA(98)(15): 123056d.
Waterbury et al., CA 80(15): 78297y.
Wilk, CA 76(17): 94410c.
Barbier and Lederer, C.R. Acad. Sci. Paris, 250, 4467 (1960), (French).
Barbier et al., Helv. Chim. Acta., 43, 1682 (1960)(German).
Borden et al., Science, 192, 894 (1976).
Butler et al., Prog. Roy. Soc. London, B. 155, 417 (1961).
Butler et al., J. Apic. Res., 12, 159 (1973).
Butler and Fairey, J. Apic. Res., 3, 65 (1964).
Callow et al., J. Apic. Res., 3, 77 (1964).
Callow and Johnston, Bee World, 41, 152 (1960).
Crewe and Velthuis, Naturwissenschaften, 67, 467 (1980).
Free, John B., Pheromones of Social Bees, Comstock Publishing, Ithaca, N.Y. (1987).
Gary, Science, 133, 1479 (1961).
Gary, Pheromones, M. C. Birch (Ed.) North Holland Publishing Co., London (1974), pp. 200-221.
Howard, et al., South-Afr. Tydskr. Chem., 34, 132 (1981).
Juska, Nature, 276, 261 (1978).
Kandil and Slessor, Can. J. Chem., 61, 1166 (1983).
Kaufman and Russey, J. Org. Chem., 30, 1320 (1965).
Lanier et al., J. Chem. Eco., 6, 677 (1980).

(List continued on next page.)

Primary Examiner—Paul Lieberman
Assistant Examiner—Linda D. Skaling
Attorney, Agent, or Firm—Willian, Brinks, Olds, Hofer, Gilson & Lione

[57] ABSTRACT

A novel combination of five queen-produced mandibular gland substances which can be used for controlling worker retinue formation around or in place of a honey bee queen Apis mellifera L. is disclosed. The composition comprises: 9-keto-2(E)-decenoic acid, R-(−)- and S-(+)-9-hydroxy-2(E)-decenoic acid, methyl p-hydroxybenzoate, and 4-hydroxy-3-methoxyphenylethanol. Each component more or less is generally weakly active alone, but the blend of five compounds in a ratio corresponding to their occurrence in gland extracts imparts activity equivalent to queen mandibular extract at a level as low as $10^{-7}$ of that present in a queen. This blend of compounds initiates the retinue response, which includes the licking and antennating behaviour that signals the presence of a dominant reproductive queen, and thereby establishes and stabilizes the social fabric of the colony.

4 Claims, 3 Drawing Sheets

OTHER PUBLICATIONS

Lombardo and Taylor, *Synthetic Communications*, 8, 463 (1978).
Millar et al., *J. Chem. Eco.*, 11, 1071 (1985).
Pain et al., *Apidologie*, 5, 319 (1974), (French).
Pain et al., *C.R. Acad. Sci. Paris*, 251, 1046 (1960), (French).
Pham et al., *Apidologie*, 13, 143 (1982), (French).
Seeley, *Behav. Ecol. Sociobiol.*, 5, 391 (1979).
Silverstein and Young, *Pest Management with Insect Sex Attractants*, Beroza, ed., (1976), pp. 1–29.
Simpson, *J. Apic. Res.*, 18, 233 (1979).
Slessor, et al., *J. Chem. Eco.*, 11, 1659 (1985).
Vaitkeviciene, *Khim. Signaly Zhivotn*, Sokolov, Ed. (1982), pp. 168–178 (Russian).
Velthuis, *Behaviour*, 41, 105 (1972).
Velthuis, *Experimental Behavioral Ecology*, (G. Fischer Verlag, Stuttgart, N.Y.) (1985), pp. 343–357.
Winston, *The Biology of the Honey Bee*, Harvard Univ. Press, Cambridge, Mass. (1987).
Winston et al., *J. Chem. Eco.*, 8, 1283 (1982).

NOVEL PHEROMONE COMPOSITION FOR USE IN CONTROLLING HONEY BEE COLONIES

FIELD OF THE INVENTION

This invention is directed to novel pheromone-type compositions which are useful in the control of honey bee colonies.

BACKGROUND OF THE INVENTION

For over twenty-five years, it has been known that the honey bee queen exerts her influence over her sister worker caste by means of semiochemicals (N. E. Gary, in *Pheromones*, M. C. Birch (Ed.) North Holland Publishing Co., London, (1974) pp. 200-221; H. H. W. Velthuis, in *Fortschritte der Zoologie*, 31, Holldobler/Lindauer (Eds.) *Experimental Behavioural Ecology*, (G. Fischer Verlag, Stuttgart, N.Y. (1985) pp. 343-357; M. L. Winston, *The Biology of the Honey Bee*, Harvard Univ. Press, Cambridge, Mass. (1987)). The most studied and best understood of the queen pheromones have been isolated from her mandibular glands. Honey bee queen mandibular complex (HQMC) is considered to be responsible for the well-known court or retinue formation that includes the licking and antennation of the honey bee queen by workers, by which they recognize the presence of their queen and transfer pheromones from her to other workers, thereby regulating many colony activities (N. E. Gary, *Science* 133, 1479 (1961); H. H. W. Velthuis, *Behaviour* 41, 105 (1972); C. G. Butler, R. K. Callow, C. G. Koster and J. Simpson, *J. Apic. Res.* 12, 159 (1973)). None of the known constituents of this gland (twenty substances have now been identified in HQMC, R. K. Callow, J. R. Chapman, and P. N. Paton, *J. Apic. Res.* 3, 77 (1964), and Simpson (4)) has been effective in eliciting full retinue behaviour. Other activities, such as suppression of queen rearing and worker ovary development, have been attributed to known mandibular gland constituents, but the responses observed have only been partly induced by these compounds, and then only at concentrations much higher than the queen could supply, implying that pheromone components are missing.

The inventors are aware of the following patents and publications which disclose bee pheromone technology in general and honey bee pheromone technology specifically:

British Patent No. 2,095,998, issued Oct. 13, 1982 to National Res. Dev. Corp.; (STEE-) Steele & Brodie Ltd., discloses honey bee pheromone compositions containing e-citral, geraniol and nerol acid as the active constituents. The use of a synthetic attractant scent (pheromone) ased on (A) (E)-citral or a mixture of (E)- and (Z)-citral, (B) geraniol and (C) nerolic acid, from which nerol and (E,E)-farnesol are practically absent, as attractants to attract a bee colony to a hive or a trap is new. New compositions usable as synthetic pheromones for a colony of honey bees have a basis of (A) E-citral or a mixture of (E)- and (Z)-citral, (B) geraniol and (C) nerolic acid, as well as opt. (D) geranium acid, 9-oxo-2-decenoic acid, honey bee food or another excipient, and are practically free of nerol and (E,E)-farnesol.

Japanese Patent No. 60,184,045, issued Sept. 19, 1985 to Nitto Electric Ind. KK, discloses new optically active acetate(s) for production of carpenter bee sex pheromone.

Mark L. Winston, Keith N. Slessor, Michael J. Smirle and Ali A. Kandil, in *J. Chem. Ecol.*, 1982, Vol. 8, No. 10, pages 1283-8, disclose the influence of a queen-produced substance, 9HDA, on swarm clustering behaviour in the honey bee.

G. Vaitkeviciene, in *Khim. Signaly Zhivotn.*, Sokolov, V. E. (Ed), 1982, pages 168-78, discloses characteristics of deutocerebral neuronal responses of the honey bee to stimulation by queen bee pheromones.

C. G. Butler, R. K. Callow and N. C. Johnston, in *Prog. Roy. Soc. Lond. B.* 155 417-432, disclose that the methyl ester of g-oxo-decenoic acid is biologically active in inhibiting queen rearing by worker honey bees and development of their ovaries.

Pheromones of Social Bees, John B. Free, Comstock Publishing Assocs. (a Division of Cornell University Press), Ithaca, N.Y.

SUMMARY OF THE INVENTION

We have recently discovered a new blend of five mandibular compounds which is highly active in retinue formation around the queen, the licking and antennating by workers of the queen by which workers recognize the queen's presence and transfer pheromones from the queen to the workers, thereby controlling many colony activities (Slessor et al. 1988). This blend, which consists of three acids: 9-keto-2(E)-decenoic acid (9ODA), and R-(−) and S-(+)-9-hydroxy-2(E)-decenoic acid (9HDA), and two aromatics: methyl p-hydroxybenzoate (HOB) and 4-hydroxy-3-methoxyphenylethanol (HVA), is significantly more active than any of its individual components, alone or in combinations of less than five components. It also is active at extremely low concentrations, down to $10^{-7}$ equivalents of a queen's mandibular glands. One of these aromatic compounds, HVA, has not been previously identified from honey bees, while another, HOB, has been identified (J. Pain, M.-F. Hugel and M. Barbier, *C. R. Acad. Sci. Paris* 251, 1046 (1960); M. Barbier, E. Lederer, T. Reichstein and O. Schindler, *Helv. Chim. Acta* 43, 1682 (1960)), but has not been considered to have pheromonal activity, except for an undocumented report (R. M. Silverstein and J. C. Young, in *Pest Management with Insect Sex Attractants*, M. Beroza (Ed.) American Chemical Society, Washington, pp. 1-29 (1976)) that HOB in combination with decenoic acids could attract swarming workers. This discovery has the potential to lead to a better understanding of the social biology of this insect, and could be of considerable economic benefit to agriculture because colony and swarm manipulation based on semiochemicals would provide better colony management, increased production and improved pollination efficacy.

The invention is directed to a novel composition useful for controlling honey bee (*Apis mellifera* L.) colonies comprising retinue response activating amounts of: (a) 9-Keto-2(E)-decenoic acid; (b) R-(−)-9-Hydroxy-2(E)-decenoic acid; (c) S-(+)-9-Hydroxy-2(E)-decenoic acid; (d) Methyl p hydroxybenzoate; and (e) 4-Hydroxy-3-methoxyphenylethanol.

The composition may comprise:

(a) 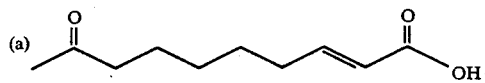

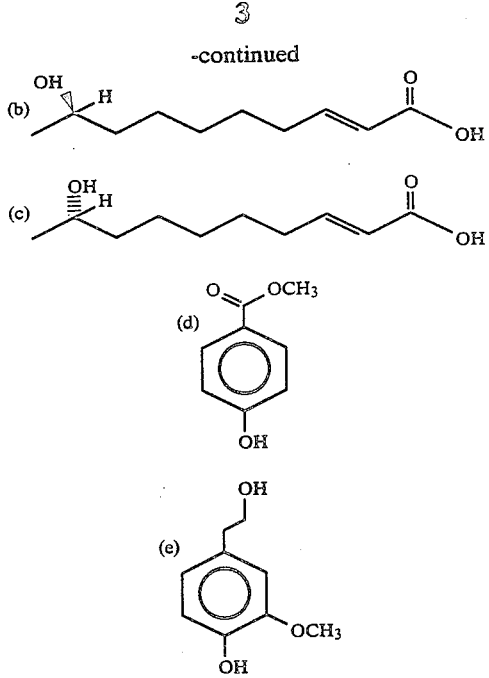

and honey bee (*Apis mellifera* L.) biologically active esters thereof.

The invention is also directed to a method of attracting a honey worker bee utilizing a composition made up of honey bee retinue response inducing amounts of one or more of the following ingredients: (a) 9-Keto-2(E)-decenoic acid; (b) R—(—)—9-Hydroxy-2(E)-decenoic acid; (c) S-(+)-9-Hydroxy-2(E)-decenoic acid; (d) Methyl p hydroxybenzoate; or (e) 4-Hydroxy-3-methoxyphenylethanol. One or more honey bee retinue response inducing esters of the specified ingredients may be used in place of the said ingredients. The five ingredients may be present in a ratio which corresponds generally with the ratio of corresponding ingredients in honey bee queen, *Apis mellifera* L., mandibular extract.

The invention is also directed to a compound useful as a component in a honey bee attractant, or controlling honey bee colony activity, namely, 4-hydroxy-3-methoxyphenylethanol.

DRAWINGS

In the drawings:

FIG. 1 depicts a plot of the relationship between dose and contact response in the pseudo-queen bioassay for natural (X———X) and synthetic (O———O) Honey Bee Queen Mandibular Complex HQMC.

FIG. 2A and 2B illustrate graphs of the persistence of worker honey bees in the pseudo-queen bioassay to natural and synthetic HQMC, as well as methanol solvent. In particular FIG. 2A illustrates a graph of cumulative proportion of worker-visits versus duration, and FIG. 2B illustrates a graph of number of worker-visits versus duration. Persistence is defined as the time spent in any visit by a worker bee entering the active ellipse during the first two minutes of a bioassay.

FIG. 3 illustrates the mean (+S.E.) number of queen cells in colonies containing a queen, blank slides, mandibular gland extract (QMC), synthetic decenoic acids (DA), and DA plus aromatics (SQMC).

DETAILED DESCRIPTION OF SPECIFIC EMBODIMENTS RELATING TO THE INVENTION

Figure 1:
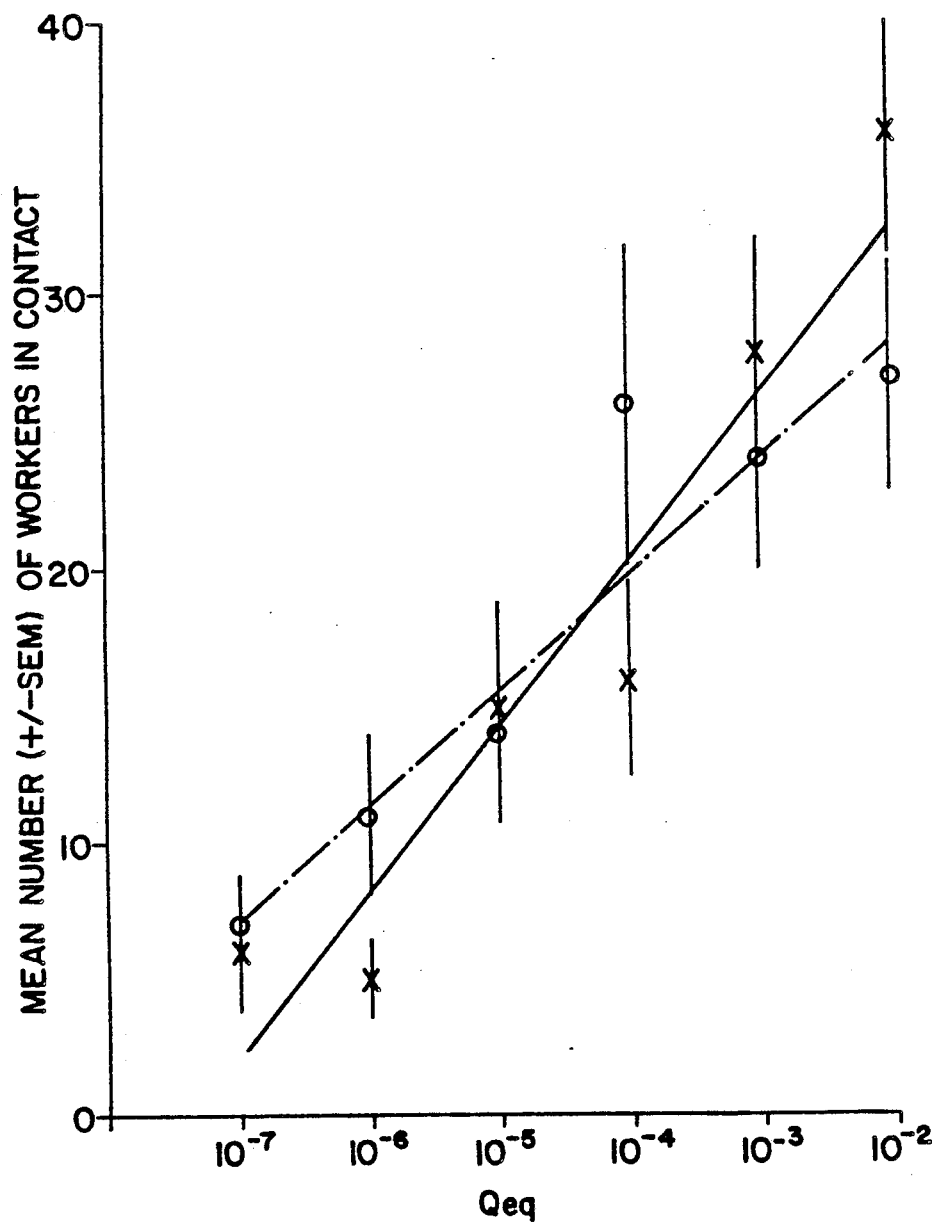

The honey bee queen mandibular complex of the invention has the following potential applications:

1. The complex can be added to preswarming queen-right colonies to increase titre of pheromone, thereby suppressing queen rearing and swarming.
2. The complex can act as a lure, alone or in combination with worker pheromones, to attract swarms for (a) increasing apiary size, (b) monitoring spread of africanized bees, and/or (c) catching swarms of africanized bees for extermination by some suitable means.
3. The complex can be used in place of the queen for shipping packages of bees.
4. The complex can replace the queen in a disposable pollination unit.
5. The complex can augment the queen in a pollination unit to stimulate foraging for pollen.
6. The complex can be used as an attractant on target crops to increase pollination efficacy.
7. The complex can be used to augment natural queen pheromone in mass queen storage, either in summer "banks" or during the winter.
8. The complex can be used to stimulate brood production early in spring for package-producing colonies.
9. The complex can be used to stimulate foraging in active colonies.

Materials and Methods

Based on the initial chemical experiments of Simpson (J. Simpson, *J. Apic. Res.* 18, 233 (1979)), and a bioassay of honey bee worker attraction (M. H. Pham, B. Roger and J. Pain, *Apidologie* 13, 143 (1982)), the inventors began a systematic separation and identification of the active component(s) present in the queen mandibular gland extract.

Bioassays

Worker bees were removed from the upper recesses of a large colony between 10:00 and 10:30 A.M., lightly narcotized with carbon dioxide, apportioned in groups of 15 into bioassay cages or arenas, and held at room temperature for 3–5 hours with access to 33% aqueous sugar syrup.

Stimuli were presented at concentrations equivalent to the queen extract being compared. Fresh stimuli were prepared each day in advance, coded, and placed randomly on drying racks. When micro-pipettes were used to deliver the stimulus, they were fixed on an incline to allow the contents to be deposited by solvent evaporation at the tips. Glass pseudo-queens were fashioned from a 7 cm length of a 1 mL Pasteur pipette (2.5 cm of the top and 5 cm of the narrowed bottom) cut and sealed at both ends. A small indentation suitable for receiving a 10 μL test stimulus was formed in the "head" end. After the solvent had evaporated, the psuedo-queens were stored in a refrigerator until immediately before a bioassay. Each group of workers was used only once, then killed by freezing, and the cages washed in hot water and air dried.

Micro-Pipette Bioassay

The wooden cages used for micro-pipette bioassays measured 10×10×6.5 cm, with one of the large sides covered with screening and the other by a sliding plexiglass door. Two micro-pipettes, one a solvent control, and the other a fraction or synthetic compound, were placed near the bottom of the cage, flush with the screen. The identity and order of the stimuli were unknown to the observer. Observations were made for 5 minutes. A positive response was recorded when a worker contacted a pipette.

Pseudo-Queen Bioassay

Bioassay cages were prepared from disposable plastic petri plates (15×2 cm). One circular hole (1.5 cm diam.) was cut into the top and covered with screening, through which the bees were fed, and another hole (1 cm diam.) was cut in the side for introducing a glass pseudo-queen into the arena. Upon introduction of the pseudo-queen stimulus, activity within the cage was recorded on video tape for 5 minutes. At 30 second intervals, the number of workers contacting the pseudo-queen and those within an "active ellipse", i.e., within one worker length of it, were recorded. These counts were summed for each replicate. The time spent by each bee within the active ellipse was used as a measure of persistence at the stimulus source. Only bees entering the ellipse during the first 2 minutes of a trial were measured for a maximum duration of 3 minutes.

Frame Bioassay

Five frames containing approximately equal amounts of bees were taken from a colony from which the queen had been removed for at least 1 hour. These frames were placed on a viewing rack on a sunny, warm (23° C.) day. Five treatments were randomly assigned and each placed in the centre of a frame. The treatment area was video-taped and bee behaviour analyzed as for the pseudo-queen bioassay. New sets of 5 frames, each set from a separate colony, were used for additional replicates.

Extracts

Initial experiments utilized laying queens which were removed from normal colonies and immobilized at −20° C. Mandibular glands were excised and macerated in hplc-grade methanol (50 μL). The mixture was centrifuged, the methanolic extract removed, a fresh portion of methanol added, and the extraction repeated to give a combined total extract of 100 μL/queen.

Analyses of Mandibular Gland Components

To a portion of extract (2–20 μL), an internal standard containing 0.66 μg of decanoic acid in methanol (2 μL) was added and the solvent removed under reduced pressure. Trimethylsilylation to facilitate gas chromatography was accomplished through addition of 5μL of bistrimethylsilyltrifluoroacetamide. The solution was agitated and left at room temperature for 40–90 minutes. Redistilled reagent grade hexane (100 μL) was added, the solution mixed and a portion (3 μL) injected in a splitless mode onto a 30 m DB-1 J & W Scientific, Inc., Rancho Cordova, Calif.) column on a Hewlett-Packard 5880 gas chromatograph (90° C. for 5 min. 10° C./min. to 200° C., isothermal for 5 min.). Integration responses were measured on a flame ionization detector calibrated with known standards for each mandibular component. Determination of the chirality of the 9-hydroxy-2(E)-decenoic acid (9HDA) was done on a 5 μL portion of the methanolic mandibular extract (K. N. Slessor, G. G. S. King, D. R. Miller, M. L. Winston, and T. L. Cutforth, *J. Chem. Ecol.* 11, 1659 (1985)).

Synthetic Pheromones

9-Keto-2(E)-decenoic acid (9ODA) (L. Lombardo and R. J. K. Taylor, *Synthetic Communications* 8, 463 (1978)), and S-(+), R-(−), and (+/−)-9HDA (A. A. Kandil and K. N. Slessor, *Can. J. Chem.* 61, 1166 (1983)), were synthesized. Methyl p-hydroxybenzoate (HOB), and 4-hydroxy-3-methoxyphenylethanol or homovanillyl alcohol (HVA) (recrystallized from ethyl acetate: 30–60° C. petroleum ether) were obtained from Sigma Chemical Co., St. Louis, Mo.

Fractionation of HQMC

A three-queen equivalent (Qeg) HQMC extract in methanol (300 μL) was solvent exchanged with heptane (2×500 μL) by two evaporations to 100 μL, after which ether (50 μL) and heptane (350 μL) were added. This solution was chromatographed on a micro-column consisting of a Pasteur pipette containing 750 mg of acid-treated silica gel prepared by thoroughly mixing Merck Kieselgel 60 (230–400 mesh) with 0.6 mL of 0.5 N $H_2SO_4$ and allowing the mixture to dry at room temperature for two days. The column was eluted to obtain ten fractions (column fractions were collected as follows: 1×1 mL of 10% ether-hexane, 2×1 mL of 25% ether-hexane, 4×1 mL of 50% ether-hexane, 2×1 mL of 75% ether-hexane, and 1×1 mL ether. Test chromatographic columns indicated that individual compounds were eluted in one, or at most two, fractions), which were analyzed by splitless capillary gas chromatography, before and after methylation with $BF_3$-methanol (K. N. Slessor, G. G. S. King, D. R. Miller, M. L. Winston and T. L. Cutforth, *J. Chem. Ecol.* 11, 1659 (1985)). In replicated micro-pipette bioassays, the ten fractions (F) were analyzed alone and in all possible binary combinations ($10^{-2}$ Qeg, n=2).

Identification of Active Components

The most striking feature of the resulting data matrix was the broad behavioural activity elicited by the binary combinations in contrast to individual fractions which were minimally active. The response when F3 or 4 was combined with F8 was consistently greater than that for other binary mixtures. The most abundant substance in F3 and 4 was unchanged by methylation, both chromatographically and in bioassay when combined with F8. Acetylation destroyed its activity and produced a substance with a greater retention time. This substance was shown by splitless capillary gas chromatography-mass spectroscopy (scgc-ms) (scgc-ms yielded a spectrum (base peak m/Z=121; 152, 65%; 194, 15%), identical to that obtained for synthetic methyl p-acetoxybenzoate) to be methyl p-acetoxybenzoate. The parent material, methyl p-hydroxybenzoate (HOB), is known in HQMC (Pain, Hugel and Barbier, (1960); Barbier, Lederer, Reichstein and Schindler, (1960)), and was shown to be present in F3 and 4 by scgc. In bioassay, bee contacts with micro-pipettes emitting HOB alone were only 9% of those observed for HQMC (n=5).

Weakly active F6 (22% that of HQMC) contained 9-keto-2(E)-decenoic acid (9ODA), the first queen pheromone to be identified (M. Barbier and E. Lederer, *C. R. Acad. Sci. Paris* 250, 4467 (1960); R. K. Callow and N. C. Johnston, *Bee World* 41, 152 (1960)). This discovery led us to test the possibility of activity when HOB and 9ODA were combined. A strong response, 52% of HQMC, was obtained to this combination, in agreement with the binary fraction bioassays and a report (Silverstein and Young, (1976)) indicating that these chemicals can produce swarm attraction. 9-Hydroxy-2(E)-decenoic acid (9HDA) was present in F7 as shown by the scgc retention time and scgc-ms of the methylated derivative. The presence of weak activity in F7 (20%) and the increase in activity when racemic 9HDA was combined with HOB (43% of HQMC) suggested the involvement of 9HDA. The decenoic acids, considered inhibitors of ovarian development (C. G. Butler, R. K. Callow and N. C. Johnston, Proc. Roy. Soc. B. 155, 417 (1965)), provided minimal response individually or in combination (4% of HQMC). The presence of 9HDA in HQMC was known (C. G. Butler and E. M. Fairey, J. Apic. Res. 3, 65 (1964)), but its involvement in queen recognition had been controversial until Winston et al. (M. L. Winston, K. N. Slessor, M. J. Smirle and A. A. Kandil, J. Chem. Ecol. 8, 1283 (1982)), showed that the chirality of 9HDA is behaviourally important and that R—(—)—9HDA can maintain queenless swarms. The enantiomeric ratio of 9HDA found in queen bees is variable, but the R—(—)—enantiomer predominates (K. N. Slessor, G. G. S. King, D. R. Miller, M. L. Winston and T. L. Cutforth, J. Chem. Ecol. 11, 1659 (1985)). Each compound, although not strongly active alone, HOB (9%), 90DA (22%), and racemic 9HDA (0% of HQMC), was now demonstrated to be involved in HQMC behaviour when combined (57% of HQMC), although the role of chirality of 9HDA remained unclear.

The activity of F8 indicated the presence of a more polar substance than any of the aforementioned compounds. This substance was unaffected by $BF_3$ methylation or catalytic hydrogenation at atmospheric pressure, but its activity and presence was completely destroyed by acetylation or bromination. Acetylation followed by scgc-ms disclosed a spectrum (scgc-ms spectrum disclosed a dominant base peak at m/Z=150; as well as 135, 20%; 137, 18%; 192, 4%; and 252, 2%. Nmr in $CD_2C_{12}$ at 400 mHz for 114 h (97,456 scans), $\delta=$ 2.01(3H, singlet, acetoxymethyl); $\delta=2.26$(3H, singlet, aryl acetoxymethyl); $\delta=2.92$(2H, triplet, J=7 Hz, benzylic methylene); $\delta=3.08$(3H, singlet, aryl ($OCH_3$); $\delta=4.26$(2H, triplet, J=7 Hz, $CH_2O$); 6.80(1H, quartet, J=2 Hz, $H_6$aryl); $\delta=6.85$(1H, doublet, J=2 Hz, $H_2$aryl); $\delta=6.94$(1H, doublet, J=8 Hz, $H_5$aryl). A 10,000 scan decoupling of the $\delta=2.92$ signal eliminated the $-0.5$ Hz coupling to $\delta=6.80$ and $\delta=6.85$ aryl hydrogen confirming these hydrogens as ortho to the ethanol side chain) reminiscent of the material observed in HQMC and thought to be 4-hydroxy-2-methoxyphenylethanol (R. M. Crewe and H. H. W. Velthuis, Naturwissenschaften 67, 467 (1980)). Synthesis of this compound as reported (A. S. Howard, J. P. Michael and M. A. Schmidt, S.-Afr. Tydskr. Chem. 34, 132 (1981). The reported structural assignments in this paper are reversed. The reader is directed to K. D. Kaufman and W. E. Russey, J. Org. Chem. 30, 1320 (1965) for the correct structural precursors) led to two hydroxymethoxyphenylethanols, the acetate derivatives of which had chromatographic retention characteristics different from the F8 HQMC component. Neither of these hydroxymethoxyphenylethanols was active, nor enhanced activity, when tested with the other materials in the micro-pipette biassay. Therefore, in November, 1986, the isomer responsible for the enhanced activity was isolated and identified from a HQMC extract of five queens that had been laying through the summer. This extract was active and contained the F8 component even though only small quantities of queen pheromone are produced in the fall (J. Pain, B. Roger and J. Theurkauff, Apidologie 5, 319 (1974)). After isolation and acetylation, we obtained only 2-3 µg of the putatively active compound in F8. High resolution 1H nuclear magnetic resonance (nmr) spectroscopy of this material (scgc-ms spectrum disclosed a dominant base peak at m/Z=150; as well as 135, 20%; 137, 18%; 192, 4%; and 252, 2%. Nmr in $CD_2C_{12}$ at 400 mHz for 114 h (97,456 scans), $\delta=2.01$(3H, singlet, acetoxymethyl); $\delta=2.26$(3H, singlet, aryl acetoxymethyl); $\delta=2.92$(2H, triplet, J=7 Hz, benzylic methylene); $\delta=3.08$(3H, singlet, aryl ($OCH_3$); $\delta=4.26$(2H, triplet, J=7 Hz, $CH_2O$); $\delta=6.80$(1H, quartet, J=2 Hz, $H_6$aryl); $\delta=6.85$ (1H, doublet, J=2 Hz, $H_2$aryl); $\delta=6.94$(1H, doublet, J=8 Hz, $H_5$aryl). A 10,000 scan decoupling of the $\delta=2.92$ signal eliminated the $-0.5$ Hz coupling to the $\delta=6.80$ and $\delta=6.85$ aryl hydrogen confirming these hydrogens as ortho to the ethanol side chain) gave a spectrum interpreted as 4-hydroxy-3-methoxyphenylethanol. Acetylation of 4-hydroxy-3-methoxyphenylethanol or homovanillyl alcohol, (HVA), provided nmr and scgc-ms spectra and retention times identical to those obtained from the acetylated derivative of HQMC present in F8. The addition of HVA to the three previously implicated compounds raised the response to 83% of that obtained from HQMC.

To confirm the activity of the complete synthetic mixture, the more sensitive pseudo-queen bioassay was employed. No individual compound elicited the full retinue response, but a combination of five compounds in a ratio comparable to that in extracts was capable of reproducing a behaviour equivalent to that evoked by HQMC extract (see Table 1 below). The enhanced activity exhibited by individual semiochemicals and partial mixtures in the pseudo-queen bioassay, in contrast to the micro-pipette bioassay, is considered to result from the use of young spring bees and the close proximity of the bees to the stimuli in the pseudo-queen experiments.

Table 1

This table tabulates the response of worker honey bees to pseudo-queens treated with with HQMC components alone and in all combinations (n=15). All treatments containing HQMC components were presented at concentrations corresponding to $10^{-3}$ Qeg. The queen extract contained HOB (13 µg)+9ODA (150 µg)+9HDA (71% R-(—)) (55 µg) +HVA (1.5 µg) per queen, arbitrarily defined as 1 Qeg and was prepared from a mixture of eight mated queens, three of which were laying, and five were received in mailing cages. Means within columns followed by the same letter are not significantly different, Tukey's multiple range test (21), P <0.05.

TABLE I

| | Mean ± SEM number of bees | |
|---|---|---|
| Treatments | Contacting Stimulus | Within Active Ellipse |
| Queen Extract ($10^{-3}$ Qeq) | 24.7 ± 3.3 a | 50.3 ± 5.7 a |
| HOB + 90DA + 9 HDA + HVA | 17.1 ± 3.4 ab | 39.8 ± 6.4 ab |
| HOB + 90DA + HVA | 13.1 ± 2.3 bc | 33.6 ± 3.7 abc |
| HOB + 9HDA + HVA | 6.1 ± 1.3 cd | 29.4 ± 4.1 bcd |
| HOB + 90DA + 9HDA | 6.7 ± 1.7 cd | 20.7 ± 3.1 cd |

TABLE I-continued

| Treatments | Mean ± SEM number of bees | |
|---|---|---|
| | Contacting Stimulus | Within Active Ellipse |
| 9ODA + 9HDA + HVA | 3.4 ± 0.6 d | 17.3 ± 2.1 cd |
| HOB + HVA | 7.6 ± 1.1 cd | 33.0 ± 3.2 abc |
| HOB + 9ODA | 9.0 ± 1.8 cd | 29.0 ± 3.3 bcd |
| 9ODA + HVA | 4.3 ± 1.1 d | 23.1 ± 3.1 bcd |
| 9ODA + 9HDA | 3.5 ± 1.0 d | 25.9 ± 3.1 bcd |
| HOB + 9HDA | 3.5 ± 0.6 d | 19.5 ± 2.1 cd |
| 9HDA + HVA | 3.9 ± 0.7 d | 21.9 ± 2.7 cd |
| 9ODA | 6.1 ± 1.3 cd | 21.3 ± 3.4 cd |
| HVA | 4.7 ± 0.9 d | 23.7 ± 4.3 bcd |
| 9HDA (76% R—(—)) | 3.5 ± 1.3 d | 16.4 ± 3.2 cd |
| HOB | 2.9 ± 0.7 d | 16.9 ± 1.8 cd |
| Methanol (solvent blank) | 1.3 ± 0.4 d | 12.0 ± 1.9 d |

Validation of Semiochemicals Eliciting Retinue Response

Several experiments were conducted to verify that the retinue response was due solely to the identified compounds. First, in the pseudo-queen bioassay, which was $10^5 \times$ more sensitive than the micro-pipette bioassay, the HQMC extract and the synthetic mixture over concentrations from $10^{-2}$ to $10^{-7}$ Qeg were not statistically different (D. G. Kleinbaum and L. L. Kupper, *Applied Regression Analysis and Other Multivariable Methods*, Duxbury Press, North Scituate, Mass. (1978)) in slope (P >0.2) and intercept (P >0.2) (see FIG. 1). Synthetics appeared to be slightly more active at $10^{-6}$ Qeg, presumably due to the diluent and anti-evaporative effects of fats, oils and other extractives in the natural HQMC extract. Synthetic queen substance was still active at or below $10^{-7}$ Qeg (ANOVA, P <0.025, n=16), the equivalent of <0.015 ng of 9ODA, in excellent agreement with Seeley's estimation of <0.1 ng of 9ODA present on a worker messenger bee (T. D. Seeley, *Behav. Ecol. Sociobiol.* 5, 391 (1979)).

FIG. 1 depicts a plot of the relationship between dose and contact response in the pseudo-queen bioassay for natural (X---------X) and synthetic (O--------O)HQMC. Table 1 gives the definition of 1 Qeg. All data has been adjusted to eliminate solvent response. Regression equations and significance for natural and synthetic HQMC, respectively, are y=46.0+6.29 log x, $r^2$ =0.90, P <0.005 and y=37.6+4.31 log x, $r^2$ =0.86, P <0.005 (22). (See reference *Applied Regression Analysis and Other Multivariable Methods* (supra.)

Secondly, a freshly prepared HQMC extract was fractionated by high performance liquid chromatography on a reverse phase column under conditions separating the components into four fractions, plus a fifth fraction that would include any late-eluting non-polar constituents. Equal responses were obtained to the reconstituted fractions, the original extract, and to the synthetic mixture. Thus, no labile or volatile component was lost in the fractionation procedure. Addition of each of the five fractions to the synthetic mixture produced no increase in response in the pseudo-queen bioassay at $10^{-3}$ Qeg (ANOVA, P >0.50, n=9).

Thirdly, both enantiomers of 9HDA were tested alone, together in a mixture approximating the natural enantiomeric composition, and in combination with the other mandibular components in the pseudo-queen bioassay. The results (see Table 2 below) demonstrate that both enantiomers of 9HDA are essential for retinue behaviour, only the fourth example of enantiomeric synergism between insect semiochemicals (J. H. Borden, L. Chong, J. A. McLean, K. N. Slessor and K. Mori, *Science* 192, 894 (1976); G. N. Lanier, A. Classon, T. Stewart, J. J. Piston and R. M. Silverstein, *J. Chem. Ecol.* 6, 677 (1980); J. G. Millar, H. D. Pierce, Jr., A. M. Pierce, A. C. Oehlschlager and J. H. Borden, *J. Chem. Ecol.* 8, 1071, (1985)).

Table 2

This table tabulates the importance of chirality of 9HDA in expression of retinue response to HQMC components by worker honey bees in the pseudo-queen bioassay (n=16). All treatments containing HQMC components were presented at concentrations corresponding to $10^{-3}$ Qeg. Means within columns followed by the same letter are not significantly different, Tukey's multiple range test (J. H. Zar, *Biostatistical Analysis*, 2nd ed. Prentice-Hall, Englewood Cliffs, N.J. (1984)), P <0.05.

| Treatments | Mean ± SEM number of bees | |
|---|---|---|
| | Contacting Stimulus | Within Active Ellipse |
| (76% R—(—))9HDA + HOB + HVA + 9ODA | 23.5 ± 2.1 a | 55.1 ± 3.5 a |
| (+)9HDA + HOB + HVA + 9ODA | 15.4 ± 2.8 ab | 38.6 ± 4.6 b |
| (—)0HDA + HOB + HVA + 9ODA | 13.4 ± 2.3 b | 36.6 ± 4.7 b |
| HOB + HVA + 9ODA | 13.9 ± 3.3 b | 34.0 ± 4.3 b |
| (76% R—(—))9HDA (57 ng) | 3.0 ± 0.7 c | 14.6 ± 2.6 c |
| S—(+)—9HDA(14 ng) | 2.7 ± 0.7 c | 14.4 ± 2.6 c |
| R—(—)—9HDA(43 ng) | 2.5 ± 0.7 c | 13.2 ± 2.1 c |
| Methanol (solvent blank) | 0.7 ± 0.3 c | 6.5 ± 1.5 c |

Persistence of the Retinue Response

Early in our work using the micro-pipette bioassay, we observed that some worker honey bees which had found the lure would not vacate their position and allow others to contact it. In the pseudo-queen bioassay, this persistent behaviour was more obvious; some bees visited the lure and stayed, while others visited and quickly departed. To demonstrate further the integrity of the complete synthetic mixture, the persistence of workers in the bioassay to the synthetic mixture was compared to HQMC extract (both at $10^{-3}$ Qeg) and to methanol solvent (see FIG. 2A and 2B which are discussed in more detail below). The bimodal persistence respones profiles to synthetic and natural extracts were different from that to the solvent, but not from each other. Twenty-five to 30% of the bees exhibited typical retinue behaviour, including prolonged antennation and licking of the lure, occasional turning away to groom their mouth parts or antennate with other bees, but no movement away from the active ellipse. The percentage of worker bees responding and their persistence is greater than those of the messenger bees described by Seeley (23); however, our experimental bees were queen-and task-deprived, which may cause an enhanced response to the queen's semiochemicals.

Figure 2:
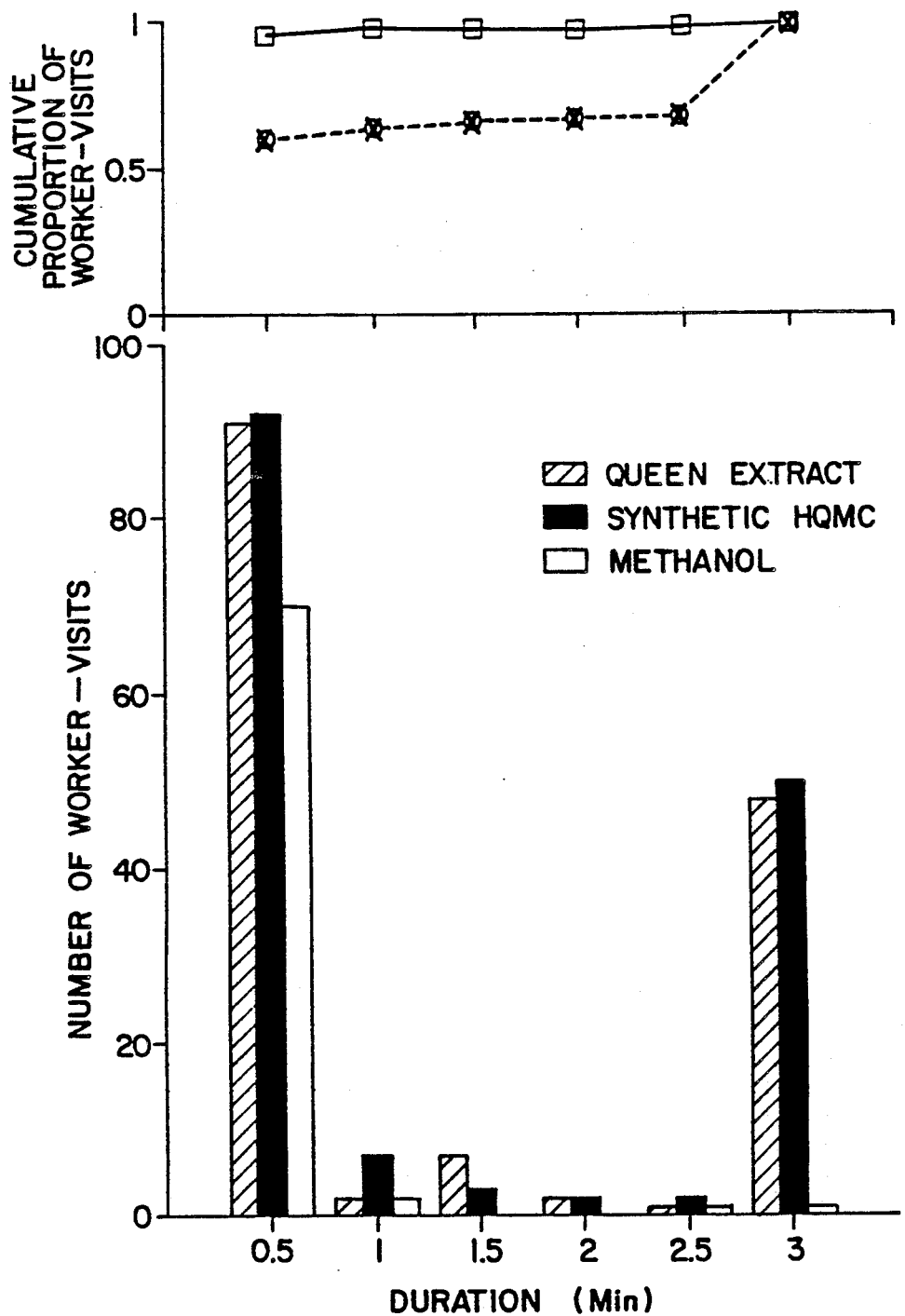

FIG. 2 illustrates a graph of the persistence of worker honey bees in the pseudo-queen bioassay to natural and synthetic HQMC, as well as methanol solvent. Persistence is defined as the time spent in any visit by a worker bee entering the active ellipse during the first two minutes of a bioassay run at $10^{-3}$ Qeg, (n=9). A Kolmogorov-Smirnov 2-tailed test (22) showed that synthetic and natural HQMC were different from solvent (P <0.001), but not significantly different from each other, P >0.10. Symbols for cumulative response curves (FIG. 2A) are: X=queen extract, 0 =synthetic HQMC and □=methanol solvent.

Hive Frame Trials

To ensure that the pseudo-queen bioassay was a valid indicator of natural retinue response, an experiment was conducted on occupied frames. Five treatments comprised of the colony's own queen, synthetic and natural HQMC, a mixture of decenoic acids, and a solvent blank were tested. The colony's own queen produced the greatest response (see Table 3 below). Synthetic and natural mandibular extracts were equally active, whereas the decenoic acids mixture or solvent showed little activity.

Table 3

This table demonstrates retinue response to the colony's own queen and pseudo-queens treated with HQMC extract, synthetic HQMC and components by worker honey bees on hive frames. Each replicate a separate colony (n=10). All treatments containing HQMC components were presented at concentrations corresponding to $10^{-2}$ Qeg (see Table 1 for composition). Means within columns followed by the same letter are not significantly different, Tukey's multiple range test, P <0.05.

| Treatments | Mean ± SEM number of bees | |
|---|---|---|
| | Contacting Stimulus | Within Active Ellipse |
| colony's own tethered queen | 86.5 ± 2.8 a | 207 ± 5 a |
| Pseudo-queen with HQMC extract | 51.6 ± 2.6 b | 146 ± 10 b |
| Pseudo-queen with synthetic HQMC | 45.1 ± 3.7 b | 160 ± 8 b |
| Pseudo-queen with 9ODA + (76% R-(-))9HDA | 12.1 ± 2.9 c | 76 ± 11 c |
| Pseudo-queen with solvent | 4.3 ± 1.3 c | 48 ± 8 c |

Queen Mandibular Gland Analyses

HQMC extracts from individual queens were analyzed for the active components and for the chirality of the 9HDA (see Table 4 below). The low levels of the aromatic components, HOB and HVA, in virgin and newly mated queens, in contrast to laying queens, may explain in part why younger queens are accepted relatively easily by a queenless colony.

Table 4

This table illustrates mandibular gland contents and 9HDA chirality of individual queen honey bees. Means within columns followed by the same letter are not significantly different, Tukey's multiple range test, P <0.05.

TABLE 4

| Queen Status | n | HQMC Content (Mean μg ± SEM) | | | | Chirality of HDA % R-(-) (mean ± SEM) |
|---|---|---|---|---|---|---|
| | | 9ODA | 9HDA | HOB | HVA | |
| Mature queens, laying 1 y | 16 | 257 ± 28 a | 105 ± 13 a | 18.1 ± 2.8 a | 3.03 ± 0.06 a | 82 ± 2 a |
| Newly mated queens | 9 | 244 ± 39 a | 51 ± 9 b | 1.8 ± 0.4 b | 0.07 ± 0.04 b | 79 ± 2 a |
| Virgin queens, 6d-old | 7 | 161 ± 22 a | 23 ± 4 b | 0.5 ± 0.1 b | <0.06 - b | 62 ± 3 b |

Body Washes of Queen Parts

The amounts of mandibular components present on queen body segments was evaluated through analysis of the amounts of 9ODA present in methanolic washes of these parts. Amounts of other HQMC constituents were often lower than detection limits, but when observed, showed ratios corresponding to their mandibular gland origin. Seven pooled samples comprising forty-one queens disclosed a mean of 181 ng 9ODA per queen for the head, 9 ng for the thorax, 16 ng for the abdomen, and 196 ng for the legs. The biologically active levels of HQMC substances present on the legs of queens (more than $10^{-3}$ Qeg) is of considerable interest in light of the attractiveness of queen "foot-print substance" (A. Juska, Nature 276, 261 (1978)).

Live Queen Bee Mandibular Extract Study

In this study, we examined the activity of live queens, mandibular extracts, the three decenoic acids in combination, and the decenoic acids plus the two aromatics in the inhibition of queen rearing and the attraction of workers during swarming.

Methods

Swarm Attraction

This study was conducted at Simon Fraser University in Burnaby, British Columbia, Canada, from July 13-17, 1987. Weather during this time was generally sunny and warm (18-27° C.), with a light wind blowing through the study sites. Experiments were performed in two large fields, with one replicate of the four treatments done at 0900 and a second at 1300 each day. The treatments consisted of (1) a live queen, and lures containing either (2) a $5 \times 10^{-2}$ dilution of the contents of the queen's mandibular gland complex (QMC), (3) a synthetic blend of the three acids and two aromatics at a concentration $5 \times 10^{-2}$ of that found in the mandibular glands (SQMC), or (4) a synthetic blend of $5 \times 10^{-2}$ of the three decenoic acids found in the queen's mandibular glands (DA).

To produce swarms, approximately 2.0 kg of workers were shaken into a wire package with a caged queen and a can of 2:1 sugar syrup; ten such packages were made up on July 10 at apiaries 30 km from the experiment site, and brought to the University. Use of these packages was rotated daily, so that no package was used more than once a day or four out of the five days. Additional workers were shaken into some packages on July 14 to keep their weight close to 2.0 kg. During the experiments, the packages were misted with water each evening, and fed additional sugar syrup until 2200 hr, when the sugar was removed until the following day's experiments were completed. To initiate an experiment, the queen was removed from four packages 60 to 90 minutes before the experiment commenced. The experiment began when 1.0 kg of workers from each of these packages were shaken onto a sheet of paper 5 m downwind from one of four sets of two posts located in the fields. Each set of posts had one post with one of the four treatments and one post with no treatment, the blank.

The posts were 2.0 m high with a crossbeam at the top from which a scale was suspended; a triangular wire mesh settling screen was suspended from the scale for the swarm to cluster on, 75-100 cm below the crossbeam. The blank post and the treatment post were situated 5 m from each other, and the swarms were shaken out equidistant from the two posts. Immediately prior to shaking each swarm out of its package, the appropriate treatment was hung on the wire mesh in a hair curler; the curlers had holes large enough for workers to pass through but small enough to contain the queen. The settling screens and curlers were used once and then discarded. The blank posts were identical to the treatment posts except that the curlers did not contain a queen or lure.

For the queen treatment, each swarm was exposed to the queen from their own package. The pseudo-queen lures for the other three treatments were fashioned from a 7 cm length of a 1 mL Pasteur pipette cut and sealed at both ends, with a small depression suitable for receiving a 10 uL liquid aliguot of treatment at one end. The queen mandibular gland extract (QMC) was prepared from the mandibular glands of eight mated queens, three of which were actively laying eggs and five which were newly mated and imported from California. Analysis of the methanolic extract indicated that 150 ug of 9ODA, 55 ug of 9HDA (71% R—(—)—, 13 ug of HOB, and 1.5 ug of HVA were present per queen. Synthetic treatments were prepared to match the queen extract as closely as possible. The synthetic decenoic acids treatment (DA) contained 147 ug of 9ODA and 57 ug of 9HDA (76% R—(—)—per queen equivalent (Qeg) in methanol. The full synthetic blend (SQMC) contained 15 ug of HOB and 1.5 ug of HVA in addition to the decenoic acids.

Stimuli were prepared in advance by administering aliquots equivalent to $5 \times 10^{-2}$ Qeg to the depression in the pseudo-queen lure. Preliminary experiments had shown SQMC lures at this concentration capable of attracting queenless swarms. The methanol solvent was evaporated at room temperature and the lures sorted according to treatment, coded, and stored at $-20°$ C. for the duration of the experiment.

To evaluate the relative efficacy of the four treatments, the weight of workers clustered on the settling screens was recorded at two minute intervals for 90 min after workers were shaken from their packages. From these data, the maximum weights obtained for each treatment could be calculated, as well as a Cluster$^{50}$ point, the time when 50% of the maximum weight was reached. For this calculation, only swarms which attracted a minimum weight of 400 g to the screen were included; this figure was chosen since it represented half of the mean weight from the queen treatment (see Table 5 below). At the end of 90 minutes, each swarm's queen was suspended from the screen to collect any remaining workers, and the swarms were then shaken back into their packages. Data were analyzed by Analysis of Variance.

Inhibition of Queen Rearing

This experiment was conducted from July 27 until Aug. 6, 1987, also at Simon Fraser University. On the first day of the experiment, forty colonies were made up by breaking down large colonies into smaller, five frame units. Each of these units consisted of two frames with eggs and young larvae covering approximately 50% of the frames, and three frames with honey, pollen, and some sealed brood. Any queen cups found on the frames were destroyed. Enough workers were included with each colony so that all of the frames would be covered with bees. Colonies were then randomly divided into five treatment groups, with eight replicates per treatment, the appropriate treatment added to each colony, and the colonies moved to a single apiary site at the University, at least 30 km from the original site where the colonies were made up. The entrances to colonies were screened for moving, and the screens kept in place for 24 hr. to minimize worker loss through disorientation.

The treatments compared in this study were (1) queenright, with the colony's own queen, (2) a blank, with no queen or pheromones added, (3) an extract from queen mandibular glands (QMC), (4) synthetic decenoic acids (DA), and (5) the decenoic acids plus the two aromatics, HOB and HVA (SQMC). The mandibular extracts were prepared from 78 mated queens, the majority of which had been laying. One queen equivalent of mandibular extract (Qeg) was found by analysis to consist of 211 ug 9ODA, 76 ug of 9HDA (83% R—(—)—, 10 ug of HOB, and 1.4 ug of HVA. The synthetic DA queen equivalent contained 210 ug of 9ODA and 75 ug of 9HDA (83% R—(—)—. The full SQMC queen equivalent contained 11 ug of HOB and 1.5 ug of HVA in addition to DA. (Note that one Qeg for this experiment differed slightly from the previous experiment, due to differences in the amounts of each component found in the mandibular glands of the queens from which the extracts were made.)

The QMC, SQMC, and DA treatments were placed in colonies on glass slides, with each slide containing $2 \times 10^{-1}$ queen eguivalents of the appropriate material. Treatments in methanol ($<20$ ul) were applied by syringe to the centre of a coded slide, the solvent evaporated at room temperature, and each set of treatments stored separately at $-20°$ C. for the duration of the experiment or until needed. The blank colonies also received a slide on the same schedule as the other treatments, but with no chemicals added. Slides were placed treatment side up on the top bar of the middle frame of each colony, and anchored in place with tacks. For the first 36 h of the experiment, slides were placed in colonies at 6 h intervals. From 36-168 h (7 days), slides were replaced at 8 h intervals. After the end of day 7, no further slides were added to colonies, since there were no larvae in colonies young enough for workers to initiate queen rearing with at that time. Thus, colonies received a rate of 0.8 Qeg/d of the appropriate treatment for the first 36 h of the experiment, and 0.6 Qeg/d from then through day 7. These values and the timing of slide replacements were chosen after preliminary experiments which suggested that a five frame colony would form a proper retinue for 24 h around a synthetic SQMC lure at a rate of between 0.6 and 0.8 Qeg/d, but not at a dose of 0.3 Qeg/d.

Colonies were examined at 2 day intervals from day 2 until day 10 for the presence of queen cells. Each frame was gently shaken to remove the workers and carefully inspected for the presence of queen cells which contained a larva or, after sealing, a pupa. By this process, the number of cells per colony could be determined. Data were first analyzed by Analysis of Variance, and where significant differences were found, a Tukey Multiple Range Test was performed to compare means between the different treatments.

Results

Swarm Attraction

In no instances did workers show any interest in the blank posts; there was no settling on the blank screen, and no clusters were initiated. Workers oriented to and clustered on the post or the settling screen where the queen or lure was hung in all tests, but only the live queen attracted the clustering workers to the settling screen 10/10 times. Workers showed the poorest attraction to the DA treatment, with only 5/10 clusters forming directly on the lure and screen; the other clusters formed on the crossbeam of the post. The QMC and SQMC treatments were intermediate, both forming clusters on the screen 8/10 times. In three tests, the DA lures attracted no workers to the screen, while the other two lure treatments failed to attract any workers to the screen one time each.

The queen treatment was also the most attractive according to weight attracted to the screen, although differences between treatments were not significant ($P > 0.05$, Table 5). The QMC and SQMC treatments were intermediate in weight, about 80% of the worker weight attracted by the live queen, while the decenoic acids showed the lowest attraction, 62% of the live queen. In three instances (one each for the queen, QMC, and SQMC treatments), more than 1.0 kg of workers were collected, probably due to drift from the other treatments or from workers which had not been collected during the previous morning's or day's experiments.

For cluster[50] time, the SQMC was closest to that of the live queen, followed by the QMC treatment (Table 5). The DA treatment was similar to the queen, but the sample size was low ($N=5$), since five of the clusters did not form on the screen. However, none of these differences were statistically significant ($P > 0.05$).

Suppression of Queen Rearing

Figure 3:
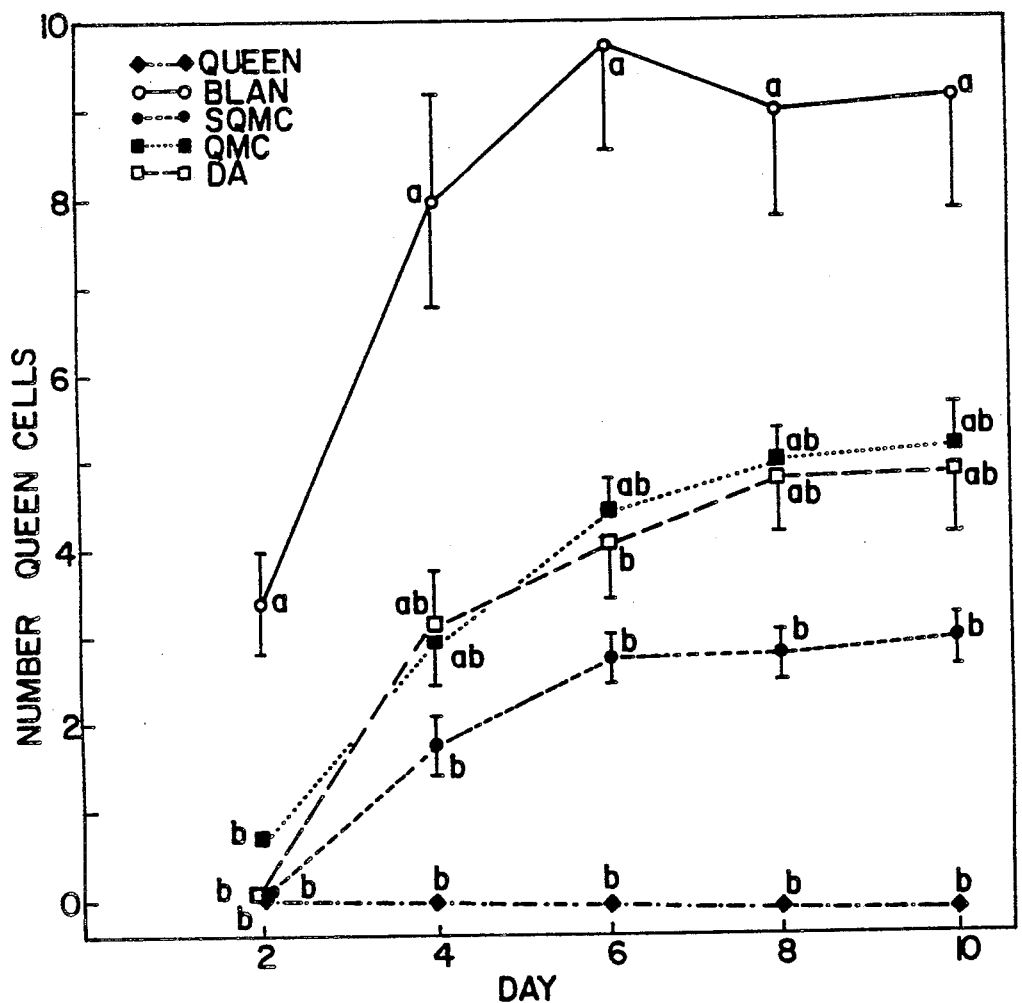

Throughout the experiment, no queen cells were found in any of the queenright colonies. Two days after queens were removed from colonies, only the blank treatment showed significantly more queen rearing than the queen ($P < 0.05$), the DA, SQMC, and QMC treatments were not significantly different from the queenright control (FIG. 3). The results from days 4, 6, 8, and 10 were essentially similar for each of these days; in all cases, the blank treatment reared significantly more queens than the queenright colonies ($P < 0.05$). For the other treatments, only the SQMC treatment consistently showed significantly less queen rearing than the blank ($P < 0.05$), but no significant differences from the queen ($P > 0.05$). The QMC and DA treatments were not significantly different from the blank or from the queen and SQMC treatments ($P > 0.05$), except for the decenoic acids on day 6 being significantly lower than the blank ($P < 0.05$).

FIG. 3 illustrates the mean ($\pm$S.E.) number of queen cells in colonies containing a queen, blank slides, mandibular gland extract (QMC), synthetic decenoic acids (DA), and DA plus aromatics (SQMC). The QMC, SQMC, and DA treatments were presented to colonies at a rate of 0.8 Queen Equivalents (Qeg) for the first 36 h, and then 0.6 Qeg until the end of day 7 (for exact dosages, see text). For each day, means followed by the same letter were not significantly different (Tukey's multiple range test, $P < 0.05$)). For each treatment, $N=8$.

Discussion

The results of these experiments have revealed a range of moderate to strong activity levels of a new, synthetic, five-component blend of queen mandibular gland pheromones in retinue formation, the inhibition of queen rearing, and attraction of workers during swarm cluster formation (Table 6). The principal conclusions from this research are:

1. While mandibular gland pheromones were active in all three functions, the live queen always showed stronger activity. Therefore, there are other queen-produced pheromones involved in these functions.

2. However, these pheromones are not produced in the mandibular glands, since the five-component blend was always equal to or better than the mandibular gland extract.

3. The combination of the two aromatics, HOB and HVA, with the three decenoic acids, 9ODA, R-(−)-HDA, and S-(+)-HDA, showed stronger activity than the decenoic acids alone. The enhanced activity of the full, five-component blend relative to the DA treatment exhibited a range of levels from a slight, qualitative enhancement of cluster formation to a moderate, quantitative enhancement of queen rearing inhibition, to a strong, highly significant enhancement of retinue formation.

It is clear from our work and previous publications involving honey bee queen pheromones that a live queen shows a higher level of activity than any extract or synthetic blend in almost all of the colony functions and worker behaviours examined. For worker attraction to swarm clusters, the queen collected the heaviest clusters (Table 5), and the queen treatment never failed to attract workers directly to her location on the settling screen. In the queen rearing experiment, the queenright colonies did not initiate any queen cells, indicating complete control of that function by a living queen compared to only partial control by mandibular extract or synthetic pheromone blends (FIG. 3). For retinue formation, a colony's own queen produced a significantly higher response than extracts or synthetics. Thus, other queen substances and/or behaviours not involving pheromones are involved in controlling these worker activities.

However, it is also clear from our work that any additional pheromones which are involved in the functions we have examined are not produced in the mandibular glands, since the five-component blend showed activity equal to or better than the mandibular extract. In retinue formation, the combination of the three decenoic acids and two aromatics (SQMC) was not qualitatively or statistically different from the QMC treatment, while the SQMC treatment showed slightly better suppression of queen rearing compared to the QMC colonies (FIG. 3), and somewhat more rapid cluster formation in the swarming experiment (Table 5), although these latter two results were not statistically different. The slight improvement in activity with the synthetic treatment in these experiments could have been due to the more complex mandibular extract being recognized as a foreign queen, or perhaps due to some diluting effect of the additional compounds in the extract on its influence on worker behaviour. At any rate, this high level of activity of the five-component synthetic mandibular blend relative to the extracts indicates that any additional pheromones involved in these functions are non-mandibular in origin, possibly produced in the queen's abdomen (Butler and Simpson 1965; Velthuis 1970).

We have also demonstrated that the three decenoic acids plus the two aromatics HOB and HVA are more active than the decenoic acids alone. In our experiments, which used the blend of 9ODA and the ratios of the two enantiomers of 9HDA found in queens, addition of the aromatics to the decenoic acids improved swarm attraction, the inhibition of queen rearing, and retinue formation (Table 6). For swarm attraction, the DA mixture showed the lowest mean weight and highest variation of workers attracted to the screens, the most instances with no workers attracted to the screens, and the most clusters forming on the post (five of ten), although these results were not statistically significant (Table 5). The clusters formed by the decenoic acids were also the most restless; workers broke up and left their clusters in three of the ten trials. In the queen rearing suppression experiment, the DA treatment was significantly lower than the blank in the number of queen cells on only one date after the second day, while the SQMC treatment was consistently lower (FIG. 3). Finally, the decenoic acids alone showed weak activity in retinue formation, while the SQMC treatment was strongly active in that function. In all cases, the DA treatment did not fully explain the activity of mandibular gland substances, but the combination of 9ODA, R-(−)-9HDA, S-(+)-9HDA, HOB, and HVA used in these experiments was sufficient to duplicate the activity of queen mandibular pheromones.

We have used 9ODA as a benchmark compound to determine the amount of mandibular pheromones present and active on queens, and found that an average of 402 ng of 9ODA can be obtained externally from full body washes of a queen, and that quantities as low as 0.015 ng of 9ODA (in combination, of course, with even lower amounts of the other mandibular pheromones) will induce retinue formation around a lure. This amount agrees with Seeley's (1979) estimate that $<0.1$ ng of 9ODA are present on messenger bees after they have contacted the queen. In contrast, an average mated queen's mandibular glands contain 257 ug of 9ODA, and we found that 120–170 ug of 9ODA per day, with the other components, would partly suppress queen rearing. While we have done dose/response curves for retinue formation, similar research is necessary to fully understand the role of mandibular gland pheromones in the other functions. Also, while it is possible that other queen mandibular gland pheromones could be active in functions which we have not yet examined, such as the inhibition of worker ovary development or attraction of drones for mating, we believe that new pheromones will be found from other parts of the queen. The search for these new pheromones should be a high priority to reach a more complete understanding of how pheromones control colony activities in this most important social insect.

Table 5

Table 5 tabulates weight and cluster time measures of worker attraction to the queen or to lures. There were no significant differences in maximum weight or Cluster$_{50}$ time between the treatments ($P>0.05$, ANOVA). $N=10$ for maximum weight; for C50, $N=9$ for queen, 8 for QMC and SQMC and 5 for DA.

| Treatment | Maximum Weight (g) during 90 min, Mean S.E. | Range of maximum weights (g) | Cluster of time (min.), Mean S.E. |
| --- | --- | --- | --- |
| Queen | 786 ± 67 | 375–1150 | 27 ± 3 |
| Mandibular Gland Extract (QMC) | 611 ± 115 | 0–1150 | 37 ± 5 |
| 5-component Synthetic Mandibular Gland (SQMC) | 625 ± 115 | 0–1150 | 30 ± 3 |
| Decenoic Acids (DA) | 490 ± 134 | 0–1150 | 26 ± 8 |

Table 6

Table 6 illustrates relative importance of a live queen, mandibular gland extract (QMC), synthetic decenic acids (DA), and DA plus aromatics (SQMC) in retinue formation, inhibition of queen rearing, and swarm attraction.

| Activity | Retinue | Inhibition of Queen Rearing | Swarm Attraction |
| --- | --- | --- | --- |
| Strong | Queen SQMC, QMC | Queen | Queen SQMC, QMC |
| Moderate |  | SQMC QMC, DA | DA |
| Slight | DA |  |  |

Conclusions

We have demonstrated that the retinue behaviour of the worker honey bee is initiated and maintained by a mixture of five constituents of the queen's mandibular glands. The presence in the queen mandibular gland secretion of 9ODA, R-(−) and S-(+)-9HDA, HOB, and the newly-identified HVA, signal the presence and dominance of the queen as the sole female reproductive in the social organization of a honey bee colony. However, while the five compound synthetic blend fully explains the activity of HQMC in retinue initiation, it is also apparent that other, non-mandibular compounds, and/or queen behaviours, may be involved in retinue initiation and in other queen controlled worker behaviours.

In addition to recognition of queen presence, this blend (or selected combinations of components) of mandibular substances may also be involved in worker orientation during swarming, suppression of worker ovary development and egg laying, inhibition of queen rearing, individual queen recognition, and a myriad of other queen-controlled activities which maintain social cohesiveness in the nest. All of these functions must be re-examined with the new chemical knowledge presented here, and we are actively pursuing such research. With the identification of queen-produced semiochemicals, a fuller understanding of honey bee society is possible, with considerable economic benefits derived from an improved ability to manage and control this most complex of social insects.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

We claim:

1. A synthetic composition comprising the following components:
   (1) 4-hydroxy-3-methoxyphenylethanol or a honey bee biologically active ester thereof; and
   (2) at least one compound selected from the group consisting of:
   (a) 9-Keto-2(E)-decenoic acid;
   (b) R-(−)-9-Hydroxy-2(E)-decenoic acid;
   (c) S-(+)-9-Hydroxy-2(E)-decenoic acid;
   (d) Methyl phydroxybenzoate; and
   honey bee biologically active esters thereof;
   the components present in amounts effective to control or attract honey bees.

2. A synthetic composition comprising:

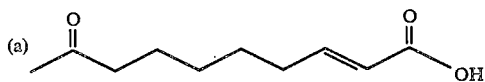

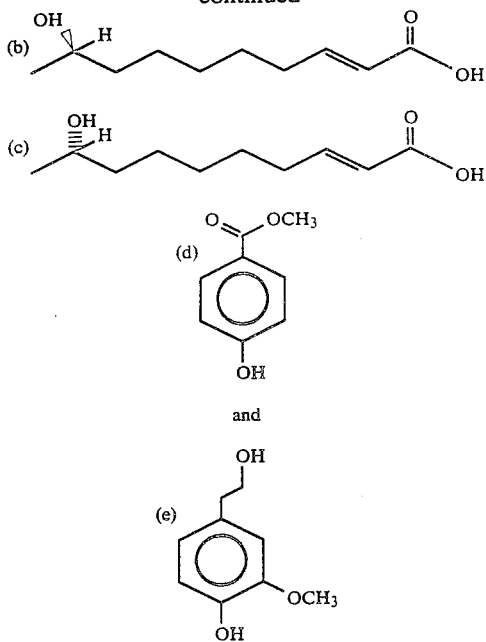

compounds (a) through (e) being present in amounts effective to control or attract honey bees.

3. A synthetic composition as defined in claim 1 comprising two compounds selected from the compounds (a) through (d) of group 2).

4. A synthetic composition as defined in claim 1 comprising three compounds selected from the compounds (a) through (d) of group 2).

UNITED STATES PATENT AND TRADEMARK OFFICE
CERTIFICATE OF CORRECTION

PATENT NO. : 4,990,331

DATED : February 5, 1991

INVENTOR(S) : Keith N. Slessor et al.

It is certified that error appears in the above-identified patent and that said Letters Patent is hereby corrected as shown below:

In column 2, lines 35 and 36, please delete "eguivalents" and substitute therefor --equivalents--.

In column 6, lines 14 and 36, please delete every occurrence of "Qeg" and substitute therefor --Qeq--.

In column 8, line 11, please delete "$CD_2C_{12}$" and substitute therefor --$CD_2Cl_2$--.

In column 8, lines 15 and 16, please delete "guartet" and substitute therefor --quartet--.

In column 8, lines 49 and 53, please delete every occurrence of "Qeg" and substitute therefor --Qeq--.

In column 9, lines 25, 31, 34, 42, and 60, please delete every occurrence of "Qeg" and substitute therefor --Qeq--.

UNITED STATES PATENT AND TRADEMARK OFFICE
CERTIFICATE OF CORRECTION

PATENT NO. : 4,990,331
DATED : February 5, 1991
INVENTOR(S) : Keith N. Slessor et al.

It is certified that error appears in the above-identified patent and that said Letters Patent is hereby corrected as shown below:

In column 10, lines 14, 47, and 68; column 11, line 41; column 12, line 34; column 13, lines 46 and 51; and column 14, lines 35, 41, 64, and 65, please delete every occurrence of "Qeg" and substitute therefor --Qeq--.

In column 14, line 48, please delete "eguivalents" and substitute therefor --equivalents--.

In column 15, lines 2 and 3; and column 16, lines 8 and 9, please delete every occurrence of "Qeg" and substitute therefor --"Qeq--.

In column 16, line 8, please delete "Eguivalents" and substitute therefor --Equivalents--.

Signed and Sealed this

Thirteenth Day of October, 1992

*Attest:*

DOUGLAS B. COMER

*Attesting Officer*     *Acting Commissioner of Patents and Trademarks*